(12) United States Patent
Tijsma et al.

(10) Patent No.: US 7,176,261 B2
(45) Date of Patent: Feb. 13, 2007

(54) ANGIOTENSIN-(1-7) ELUTING POLYMER-COATED MEDICAL DEVICE TO REDUCE RESTENOSIS AND IMPROVE ENDOTHELIAL CELL FUNCTION

(75) Inventors: Edze Jan Tijsma, Maastricht (NL); Anita Driessen-Levels, Reuver (NL); Marc Hendriks, Brunssum (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/256,582

(22) Filed: Oct. 21, 2005

(65) Prior Publication Data

US 2006/0088572 A1 Apr. 27, 2006

Related U.S. Application Data

(60) Provisional application No. 60/621,462, filed on Oct. 21, 2004.

(51) Int. Cl.
- C08F 20/10 (2006.01)
- A61K 38/08 (2006.01)
- A61F 2/04 (2006.01)

(52) U.S. Cl. ............ 525/330.3; 514/2; 623/1.15; 424/426; 604/500

(58) Field of Classification Search ............ None
See application file for complete search history.

(56) References Cited

U.S. PATENT DOCUMENTS

| | | | |
|---|---|---|---|
| 4,629,755 A * | 12/1986 | Kanaoka et al. ............ 524/415 |
| 4,961,532 A * | 10/1990 | Tangney ............ 239/60 |
| 5,834,432 A | 11/1998 | Rodgers et al. |
| 5,955,430 A | 9/1999 | Rodgers et al. |
| 6,140,127 A | 10/2000 | Sprague |
| 6,235,766 B1 | 5/2001 | Heitsch et al. |
| 6,268,364 B1 | 7/2001 | Memoli et al. |
| 6,429,222 B2 | 8/2002 | Heitsch et al. |
| 6,444,646 B1 | 9/2002 | Rodgers et al. |
| 6,538,144 B2 | 3/2003 | Heitsch |
| 6,569,441 B2 | 5/2003 | Kunz et al. |
| 6,599,928 B2 | 7/2003 | Kunz et al. |
| 6,663,881 B2 | 12/2003 | Kunz et al. |
| 6,720,350 B2 | 4/2004 | Kunz et al. |
| 6,770,729 B2 | 8/2004 | Van Antwerp |
| 2001/0037145 A1 * | 11/2001 | Guruwaiya et al. ........ 623/1.15 |
| 2002/0193336 A1 | 12/2002 | Elkins et al. |
| 2003/0073237 A1 | 4/2003 | Roks et al. |
| 2004/0127978 A1 * | 7/2004 | Sparer et al. ............ 623/1.46 |
| 2005/0119180 A1 | 6/2005 | Roks et al. |
| 2005/0142130 A1 * | 6/2005 | Roks et al. ............ 424/94.64 |
| 2005/0214339 A1 * | 9/2005 | Tang et al. ............ 424/423 |

FOREIGN PATENT DOCUMENTS

| | | |
|---|---|---|
| EP | 0533084 A1 | 3/1993 |
| EP | 1258258 A1 | 11/2002 |
| EP | 1348440 A1 | 10/2003 |
| JP | 63280701 * | 11/1988 |
| JP | 04317025 * | 11/1992 |
| WO | WO 99/09192 | 2/1999 |
| WO | WO 00/68226 | 11/2000 |
| WO | WO 01/49325 A2 | 7/2001 |
| WO | WO 03/039434 A2 | 5/2003 |
| WO | WO 03/072059 A2 | 9/2003 |
| WO | WO 03/082318 A1 | 10/2003 |

OTHER PUBLICATIONS

Erdos E.G. et al., Products of angiotensin I hydrolysis by human cardiac enzymes potentiate bradykinin. J. Mol. Cell. Cardiol. 34:1569-1576, 2002.
Handa R.K. Angiotensin-(1-7) can interact with the rat proximal tubule AT4 receptor system. Am. J. Physiol. 277:F75-F83, 1999.
Lacher N.A. et al. Separation and detection of angiotensin peptides by Cu(II) complexation and capillary electrophoresis with UC and electrochemical detection. Electrophoresis 23:1577-1584, 2002.
Loot A.E. et al., Angiotensen-(1-7) attenuates the development of heart failure after myocardial infarction in rats. Circulation 105:1548-1550, 2002.
Strawn WB, et al., Angiotensin-(1-7) reduces smooth muscle growth after vascular injury. Hypertension 33:207-211, 1999.

* cited by examiner

*Primary Examiner*—Cecilia J. Tsang
*Assistant Examiner*—Christina M. Bradley
(74) *Attorney, Agent, or Firm*—K&L Gates, LLP (57) ABSTRACT

Medical devices with polymer coatings designed to control the release of angiotensin-(1-7) receptor agonists from medical devices are disclosed. The present application also discloses providing vascular stents with angiotensin-(1-7) receptor agonist-containing controlled-release coatings. Methods for treating or inhibiting post-stent implantation restenosis as well as improving vascular endothelial function in patients are also provided.

27 Claims, 8 Drawing Sheets

FIG. 4
- ◆ 150 μg 20% ang(1-7) in C45; 60 μg C45
- ● 150 μg 20% ang(1-7) in C45; 300 μg C45
- ✕ 150 μg 20% ang(1-7) in C45

FIG. 5 ◆ 400 μg 20% ang(1-7) in C45; 350 μg PBMA

FIG. 6A
— ● — 600 µg 10% ang(1-7) in C45; 300 µg PBMA
— × — 600 µg 10% ang(1-7) in C45; 300 µg PBMA FIG. 6B
— ● — 600 µg 20% ang(1-7) in C45; 100 µg PBMA
— × — 600 µg 20% ang(1-7) in C45; 300 µg PBMA

*: p 0.01 vs. bare (one-way ANOVA, LSD-corrected)

FIG. 8B

*: p 0.05 vs. bare (one-way ANOVA, LSD-corrected)

ANGIOTENSIN-(1-7) ELUTING POLYMER-COATED MEDICAL DEVICE TO REDUCE RESTENOSIS AND IMPROVE ENDOTHELIAL CELL FUNCTION

CROSS REFERENCE TO RELATED APPLICATIONS

This application claims priority under 35 U.S.C. §119(e) to U.S. Provisional Patent Application No. 60/621,462 filed Oct. 21, 2004.

FIELD OF THE INVENTION

This invention relates generally to preventing restenosis after vascular stent implantation by delivering anti-restenotic compounds to the treatment site. More specifically the present invention provides for suppression of vascular smooth muscle cell proliferation by delivering to the treatment site agonists of the angiotensin-(1-7) receptor. More specifically the present invention provides drug-eluting vascular stents with coatings of angiotensin-(1-7) peptide-containing controlled-release polymers. Additionally the present invention provides release of angiotensin-(1-7) receptor agonists from coated stents to inhibit restenosis and improve vascular endothelial cell function.

BACKGROUND OF THE INVENTION

Medical devices are used for myriad purposes on and throughout an animal's body. They can be simple ex vivo devices such as adhesive bandages, canes, walkers and contact lenses or. complex implantable devices including pacemakers, heart valves, vascular stents, catheters and vascular grafts. Implantable medical devices must be biocompatible to prevent inducing life threatening adverse physiological responses between the implant recipient and device.

Cardiovascular disease, specifically atherosclerosis, remains a leading cause of death in developed countries. Atherosclerosis is a multifactorial disease that results in a narrowing, or stenosis, of a vessel lumen. Briefly, pathologic inflammatory responses resulting from vascular endothelium injury causes monocytes and vascular smooth muscle cells (VSMCs) to migrate from the sub endothelium and into the arterial wall's intimal layer. There the VSMC proliferate and lay down an extracellular matrix causing vascular wall thickening and reduced vessel patency.

Cardiovascular disease caused by stenotic coronary arteries is commonly treated using either coronary artery by-pass graft (CABG) surgery or angioplasty. Angioplasty is a percutaneous procedure wherein a balloon catheter is inserted into the coronary artery and advanced until the vascular stenosis is reached. The balloon is then inflated restoring arterial patency. One angioplasty variation includes arterial stent deployment. Briefly, after arterial patency has been restored, the balloon is deflated and a vascular stent is inserted into the vessel lumen at the stenosis site. The catheter is then removed from the coronary artery and the deployed stent remains implanted to prevent the newly opened artery from constricting spontaneously. However, balloon catheterization and stent deployment can result in vascular injury ultimately leading to VSMC proliferation and neointimal formation within the previously opened artery. This biological process whereby a previously opened artery becomes re-occluded is referred to as restenosis.

The introduction of intracoronary stents into clinical practice has dramatically changed treatment of obstructive coronary artery disease. Since having been shown to significantly reduce restenosis as compared to percutaneous transluminal coronary angioplasty (PTCA) in selected lesions, the indication for stent implantation was been widened substantially. As a result of a dramatic increase in implantation numbers worldwide in less selected and more complex lesions, in-stent restenosis (ISR) has been identified as a new medical problem with significant clinical and socioeconomic implications. The number of ISR cases is growing: from 100,000 patients treated worldwide in 1997 to an estimated 150,000 cases in 2001 in the United States alone. ISR is due to a vascular response to injury, and this response begins with endothelial denudation and culminates in vascular remodeling after a significant phase of smooth muscle cell proliferation.

At least four distinct phases of reaction can be observed in ISR: thrombosis, inflammation, proliferation, and vessel remodeling. There is a wide spectrum of conventional catheter-based techniques for treatment of ISR, ranging from plain balloon angioplasty to various atherectomy devices and repeat stenting. One possible method for preventing restenosis is the administration of anti-inflammatory compounds that block local invasion/activation of monocytes thus preventing the secretion of growth factors that may trigger VSMC proliferation and migration. Other potentially anti-restenotic compounds include anti-proliferative agents such as chemotherapeutics including rapamycin and paclitaxel. However, anti-inflammatory and anti-proliferative compounds can be toxic when administered systemically in anti-restenotic-effective amounts. Furthermore, the exact cellular functions that must be inhibited and the duration of inhibition needed to achieve prolonged vascular patency (greater than six months) is not presently known. Moreover, it is believed that each drug may require its own treatment duration and delivery rate. Therefore, in situ, or site-specific drug delivery using anti-restenotic coated stents has become the focus of intense clinical investigation. Once the coated stent is deployed, it releases the anti-restenotic agent directly into the tissue thus allowing for clinically effective drug concentrations to be achieved locally without subjecting the recipient to side effects associated with systemic drug delivery. Moreover, localized delivery of anti-proliferative drugs directly at the treatment site eliminates the need for specific cell targeting technologies.

Angiotensin II (Ang II) has been implicated in the development of restenosis through several mechanisms, and thus control of the renin-angiotensin system (RAS) is a potential target for its prevention. Ang II is produced as a circulating hormone by the angiotensin I (Ang I) converting enzyme (ACE). Stimulation of the angiotensin type 1 (AT1) receptor by Ang II has been shown to be associated with stimulation of cell migration and proliferation in several in vitro and in vivo models including stimulation of extracellular matrix deposition and collagen I, III and IV and fibronectin by VSMCs; stimulation of inflammation; and stimulation of intracellular formation of reactive oxygen species. In addition, AT1 stimulation has been shown to induce changes related to endothelial dysfunction.

Selective AT1 receptor blockade would thus be a potentially beneficial approach as it would inhibit the deleterious effects of $AT_1$ receptor activation. However, rather than targeting $AT_1$ receptor blockade, therapeutic intervention has primarily focused on reducing the production of Ang II by the action of ACE. The effect of ACE inhibitors on the prevention of restenosis has been investigated in two large clinical trials of the ACE inhibitor cilazapril involving more than 2,000 patients. After six months of treatment, no significant differences were seen in the incidence of restenosis between cilazapril and placebo. The inhibition of the conversion of Ang I to Ang II by ACE inhibitors was not successful in these trials and several explanations may therefore be put forward. First, the ACE inhibitor dose may have been too low to obtain sufficient ACE inhibition; high-dose ACE inhibition seems to be more effective than low dose ACE inhibition. Next, the rise in renin and Ang I that occurs when Ang II no longer suppresses renin release may, in part, overcome ACE inhibition. Third, ACE upregulation is known to occur both as a consequence of chronic ACE inhibitor therapy and during the progression of cardiovascular diseases. Finally, in vitro studies have shown that there are alternative enzymes capable of converting Ang I into Ang II. The most important of these is the serine protease chymase.

Compared with ACE inhibitors, angiotensin receptor blockers exert additional effects on the pathophysiological processes which lead to restenosis. Angiotensin receptor antagonists may affect several mechanisms involved in neointimal hyperplasia such as decreasing circulating cytokine and growth factor levels and reducing neutrophil activation. First results of using angiotensin receptor blockers after stent implantation indicated favorable results could be obtained in the prevention of in-stent restenosis through a systemic pharmacological approach (Wilensky R. L. Angiotensin-receptor blockers: Revival of the systemic prevention of restenosis? Cardiovasc. Drugs Ther. 17:63–73, 2003). This VaIPREST trial was the first randomized, placebo-controlled study to have evaluated the effect of an angiotensin receptor blocker on in-stent restenosis in a moderate number of patients. The VaIPREST trial was recently supplemented by the VALVACE trial (Peters S., et al. Valsartan versus ACE inhibition after bare metal stent implantation—results of the VALVACE trial. Int. J. Cardiol. 98:331–335, 2005). Similar to the results of the VaIPREST trial, the VALVACE trial demonstrated an impressive reduction of in-stent restenosis in comparison to ACE inhibition. These initial trials suggest that angiotensin receptor blocker therapy my be effective as an add-on therapy to drug-eluting stent.

Angiotensin-(1-7) (Ang-(1-7)), a heptapeptide biologically active member of the renin-angiotensin peptide family, antagonizes the RAS system at various levels. Being a substrate for ACE, Ang-(1-7) competes with Ang I and bradykinin for degradation, thereby inhibiting Ang II formation and augmenting bradykinin activity. Ang-(1-7) has also been found to block the deleterious actions of Ang II through a noncompetitive blockade of $AT_1$ receptors and direct stimulation of angiotensin type 2 ($AT_2$) receptors. Although ACE inhibitors were originally developed to suppress the formation of Ang II, part of their beneficial effect in cardiovascular diseases may be attributed to the resultant elevation in Ang-(1-7) levels. ACE inhibitor treatment, although having limited effects on the circulating amount of Ang II, increases Ang-(1-7) levels 10–to 25-fold.

Intravenous infusion of Ang-(1-7) inhibited smooth muscle cell proliferation associated with balloon-catheter injury (Strawn W. B. et al. Angiotensin(1-7) reduces smooth muscle growth after vascular injury, Hypertension 33:207–11, 1999). Ang-(1-7) also opposes the mitogenic response to Ang II in cultured VSMCs. Further, Ang-(1-7), through interaction with its recently discovered Ang-(1-7) receptor, has a vasodilatory effect by way of stimulating nitric oxide release.

Human clinical studies on stent-based anti-restenotic delivery have demonstrated excellent short-term anti-restenotic effectiveness. However, side effects including vascular erosion have also been seen. Vascular erosion can lead to stent instability and further vascular injury. Furthermore, the extent of cellular inhibition may be so extensive that normal re-endothelialization will not occur. The endothelial lining is essential for maintaining vascular elasticity and as an endogenous source of nitric oxide. Therefore, compounds that exert localized anti-restenotic effects while minimizing vascular and cellular damage are essential for the long-term success of drug delivery stents. Moreover, it would be beneficial if these compounds would improve vascular endothelial cell function.

SUMMARY OF THE INVENTION

The present invention is directed providing medical devices, such as stents, with controlled-release drug-eluting polymer coatings capable of inhibiting restenosis and improving vascular endothelial cell function. Specifically, the vascular stents made in accordance with teachings of the present invention inhibit vascular smooth muscle cell proliferation, and therefore restenosis, by providing agonists of the angiotensin-(1-7) (Ang-1–7)) receptor to the site of vascular injury. Additionally, the Ang-(1-7) coated medical devices of the present invention improve vascular endothelial cell function.

In one embodiment of the device of the present invention, a medical device is provided comprising a stent having a generally cylindrical shape comprising an outer surface, an inner surface, a first open end and a second open end, a controlled-release coating comprising an amphiphilic copolymer and at least one angiotensin-(1-7) (Ang-(1-7)) receptor agonist wherein at least one of said inner or outer surfaces are adapted to deliver an effective amount of said at least one Ang-(1-7) receptor agonist to a tissue of a mammal; and wherein vascular endothelial cell function is improved and/or restenosis is inhibited.

In an embodiment of the device of the present invention, the at least one Ang-(1-7) receptor agonist is a peptide having the amino acid sequence of SEQ ID NO. 1 and the medical device is a vascular stent.

In another embodiment of the device of the present invention, the at least one Ang-(1-7) receptor agonist is present on the said inner surface and the outer surface of the vascular stent. In another embodiment the amphiphilic copolymer comprises a PEG methacrylate-cyclohexyl methacrylate copolymer. In yet another embodiment the stent further comprises a primer coat, such as a parylene primer coat, and/or a polymer topcoat comprising a PEG methacrylate-cyclohexyl methacrylate copolymer or poly(butyl methacrylate).

In yet another embodiment of the device of the present invention, the Ang-(1-7) receptor agonist peptide is in a concentration of between approximately 0.1% to 99% by weight of peptide-to-polymer.

In one embodiment of the device of the present invention, a vascular stent for inhibiting restenosis in a mammal is provided comprising stent having a generally cylindrical shape comprising an outer surface, an inner surface, a first open end and a second open end, a controlled-release coating comprising a PEG methacrylate-cyclohexyl methacrylate copolymer and an anti-restenotic amount of an Ang-(1-7) receptor agonist peptide having the amino acid sequence of SEQ ID NO. 1 and a PEG methacrylate-cyclohexyl methacrylate copolymer topcoat wherein the vascular stent deliver an effective amount of said Ang-(1-7) receptor agonist to a tissue of a mammal; and wherein vascular endothelial cell function is improved and/or restenosis is inhibited. The vascular stent can optionally further comprise a primer coat.

In an embodiment of the method of the present invention, a method for inhibiting restenosis in a mammal comprises providing a vascular stent having a controlled-release coating thereon wherein said coating comprises an amphiphilic copolymer and an effective amount of at least one Ang-(1-7) receptor agonist; and inhibiting restenosis in said mammal.

In an embodiment of the method for inhibiting restenosis of the present invention, the at least one Ang-(1-7) receptor agonist is a peptide having the amino acid sequence of SEQ ID NO. 1 and the medical device is a vascular stent.

In another embodiment of the method for inhibiting restenosis of the present invention, the at least one Ang-(1-7) receptor agonist is present on the said inner surface and the outer surface of the vascular stent. In another embodiment the amphiphilic copolymer comprises a PEG methacrylate-cyclohexyl methacrylate copolymer. In yet another embodiment the stent further comprises a primer coat and/or a polymer topcoat.

In yet another embodiment of the method for inhibiting restenosis of the present invention, the Ang-(1-7) receptor agonist peptide is in a concentration of between approximately 0.1% to 99% by weight of peptide-to-polymer.

In one embodiment of the present invention, a method for improving endothelial cell function in a mammal comprises providing a vascular stent having a controlled-release coating thereon wherein the coating comprises an amphiphilic copolymer and an effective amount of at least one Ang-(1-7) receptor agonist and improving vascular endothelial cell function in said mammal.

In an embodiment of the method for improving vascular endothelial cell function of the present invention, the at least one Ang-(1-7) receptor agonist is a peptide having the amino acid sequence of SEQ ID NO. 1 and the medical device is a vascular stent.

In another embodiment of the method for improving vascular endothelial cell function of the present invention, the at least one Ang-(1-7) receptor agonist is present on the said inner surface and the outer surface of the vascular stent. In another embodiment the amphiphilic copolymer comprises a PEG methacrylate-cyclohexyl methacrylate copolymer. In yet another embodiment the stent further comprises a primer coat and/or a polymer topcoat.

In yet another embodiment of the method for improving vascular endothelial cell function of the present invention, the Ang-(1-7) receptor agonist peptide is in a concentration of between approximately 0.1% to 99% by weight of peptide-to-polymer.

In an embodiment of the present invention, a method is provided for treating impaired vascular endothelial cell function in a mammal comprising implanting a stent having a controlled release coating and an effective amount of Ang-(1-7) disposed on at least one surface of the medical device at a treatment site in a vessel lumen and releasing the Ang-(1-7) from the surface of the stent such that vascular endothelial cell function is improved at the treatment site.

BRIEF DESCRIPTION OF THE FIGURES

FIG. 2 a–d depict cross sections of the various coating configurations used to provide vascular stents with the controlled release coatings made in accordance with the teachings of the present invention.

FIG. 6 a and b graphically depict in vitro release kinetics of Ang-(1-7)-coated stents implanted in pig coronary arteries that were constructed according to the methods of the present invention.

FIG. 8 depicts quantitative histology (FIG. 8A, neointimal area.

FIG. 11 depicts morphometry of pig coronary arteries (11A, neointimal area; 11B, percent stenosis) after implantation of bare stents, C45-coated stents (polymer), slow-release C45-Ang-(1-7) coated stents (slow release) and fast-release C45-Ang-(1-7) coated stents (fast release) according to the teachings of the present invention.

DEFINITION OF TERMS

Prior to setting forth the invention, it may be helpful to an understanding thereof to set forth definitions of certain terms that will be used hereinafter:

Amphiphilic: As used herein "amphiphilic" refers to a molecule having a hydrophilic ('water loving', polar) part and a hydrophobic ('water hating', non-polar) part.

Animal: As used herein "animal" shall include mammals, fish, reptiles and birds. Mammals include, but are not limited to, primates, including humans, dogs, cats, goats, sheep, rabbits, pigs, horses and cows.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero-order kinetics), that is the drug is released in even amounts over a predetermined time (with or without an initial burst phase) or may be a gradient release. A gradient release implies that the amount of drug released from the device surface changes over time.

Compatible: As used herein "compatible" refers to a composition possessing the optimum, or near optimum combination of physical, chemical, biological and drug release kinetic properties suitable for a controlled release coating made in accordance with the teachings of the present invention. Physical characteristics include durability and elasticity/ductility, chemical characteristics include solubility and/or miscibility and biological characteristics include biocompatibility. The drug release kinetics may be either near zero-order or a combination of first and zero-order kinetics.

Copolymer: As used here in a "copolymer" will be defined as ordinarily used in the art of polymer chemistry. A copolymer is a macromolecule produced by the simultaneous or step-wise polymerization of two or more dissimilar units such as monomers. Copolymer shall include bipolymer (two dissimilar units) terpolymer (three dissimilar units) etc.

Drug(s): As used herein "drug" shall include any bioactive compound having a therapeutic effect in an animal.

Treatment Site: As used herein "treatment site" shall mean a vascular occlusion, vascular plaque, an aneurysm site or other vascular-associated pathology.

DETAILED DESCRIPTION OF THE INVENTION

The present invention is directed providing medical devices, such as stents, with controlled-release drug-eluting polymer coatings capable of inhibiting restenosis and improving vascular endothelial cell function. Specifically, the vascular stents made in accordance with teachings of the present invention inhibit vascular smooth muscle cell proliferation, and therefore restenosis, by providing agonists of the angiotensin-(1-7) (Ang-1–7)) receptor to the site of vascular injury. Additionally, the Ang-(1-7) coated medical devices of the present invention improve vascular endothelial cell function.

A particular embodiment of the present invention is the use agonists of the Ang-(1-7) receptor for coating vascular stents. Exemplary Ang-(1-7) agonists include, but are not limited to, the peptide Ang-(1-7) having the amino acid sequence of SEQ ID NO. 1, and biologically active analogues and derivatives thereof; D-alanine$^7$-Ang-(1-7); D-proline$^7$-Ang-(1-7) and AVE0991.

Angiotensin-(1-7) blocks angiotensin II activity, a protein implicated in the development of restenosis, and inhibits smooth muscle cell proliferation, a hallmark of restenosis. One embodiment of the present invention provides vascular stents coated with the heptapeptide Ang-(1-7) (SEQ ID NO. 1). SEQ ID NO. 1 Asp Arg Val Tyr lie His Pro Alternatively, potent non-peptide compounds have been described that are used as agonists of Ang-(1-7) receptors and mimic the biological action of Ang-(1-7). Specific 1-(p-thienylbenzyl)imidazoles and corresponding salts, such as those described in U.S. Pat. No. 6,235,766, which is hereby incorporated by reference in its entirety, have the advantage that they may not be subject to the metabolic degradation. Specifically, see column 1 beginning at line 58 through column 4 line 65. More specifically see column 4 line 68 through column 6 line 12 for specific examples of compositions. Therefore additional embodiments of the present invention include coating vascular stents with non-peptide Ang-(1-7) receptor agonists. Because of the stimulation of the production and/or release of these vasorelaxant, antithrombotic, and cardioprotective compounds, Ang-(1-7) receptor agonists are valuable pharmaceuticals for the treatment of restenosis.

Vascular stents present a particularly unique challenge for the medical device coating scientist. Vascular stents (hereinafter referred to as "stents") must be flexible, expandable, biocompatible and physically stable. Stents are used to relieve the symptoms associated with coronary artery disease caused by occlusion in one or more coronary artery. Occluded coronary arteries result in diminished blood flow to heart muscles causing ischemia induced angina and in severe cases myocardial infarcts and death. Stents are generally deployed using catheters having the stent attached to an inflatable balloon at the catheter's distal end. The catheter is inserted into an artery and guided to the deployment site. In many cases the catheter is inserted into the femoral artery or of the leg or carotid artery and the stent is deployed deep within the coronary vasculature at an occlusion site.

Vulnerable plaque stabilization is another application for coated drug-eluting vascular stents. Vulnerable plaque is composed of a thin fibrous cap covering a liquid-like core composed of an atheromatous gruel. The exact composition of mature atherosclerotic plaques varies considerably and the factors that affect an atherosclerotic plaque's make-up are poorly understood. However, the fibrous cap associated with many atherosclerotic plaques is formed from a connective tissue matrix of smooth muscle cells, types I and III collagen and a single layer of endothelial cells. The atheromatous gruel is composed of blood-borne lipoproteins trapped in the sub-endothelial extracellular space and the breakdown of tissue macrophages filled with low density lipids (LDL) scavenged from the circulating blood. (G. Pasterkamp and E. Falk. 2000. Atherosclerotic Plaque Rupture: An Overview. J. Clin. Basic Cardiol. 3:81–86). The ratio of fibrous cap material to atheromatous gruel determines plaque stability and type. When atherosclerotic plaque is prone to rupture due to instability it is referred to as "vulnerable" plaque. Upon rupture the atheromatous gruel is released into the blood stream and induces a massive thrombogenic response leading to sudden coronary death. Recently, it has been postulated that vulnerable plaque can be stabilized by stenting the plaque. Moreover, vascular stents having a drug-releasing coating composed of matrix metalloproteinase inhibitor dispersed in, or coated with (or both) a polymer may further stabilize the plaque and eventually lead to complete healing.

Treatment of aneurysms is another application for drug-eluting stents. An aneurysm is a bulging or ballooning of a blood vessel usually caused by atherosclerosis. Aneurysms occur most often in the abdominal portion of the aorta. At least 15,000 Americans die each year from ruptured abdominal aneurysms. Back and abdominal pain, both symptoms of an abdominal aortic aneurysm, often do not appear until the aneurysm is about to rupture, a condition that is usually fatal. Stent grafting has recently emerged as an alternative to the standard invasive surgery. A vascular graft containing a stent (stent graft) is placed within the artery at the site of the aneurysm and acts as a barrier between the blood and the weakened wall of the artery, thereby decreasing the pressure on the artery. The less invasive approach of stent-grafting aneurysms decreases the morbidity seen with conventional aneurysm repair. Additionally, patients whose multiple medical comorbidities make them excessively high risk for conventional aneurysm repair are candidates for stent-grafting. Stent grafting has also emerged as a new treatment for a related condition, acute blunt aortic injury, where trauma causes damage to the artery.

Once positioned at the treatment site the stent or graft is deployed. Generally, stents are deployed using balloon catheters. The balloon expands the stent gently compressing it against the arterial lumen clearing the vascular occlusion or stabilizing the aneurysm. The catheter is then removed and the stent remains in place permanently. Most patients return to a normal life following a suitable recovery period and have no reoccurrence of coronary artery disease associated with the stented occlusion. However, in some cases the arterial wall's intima is damaged either by the disease process itself or as the result of stent deployment. This injury initiates a complex biological response culminating in vascular smooth muscle cell hyperproliferation and occlusion, or restenosis, and vascular endothelial cell damage at the stent site.

Recently significant efforts have been devoted to preventing restenosis. Several techniques including brachytherapy, excimer laser, and pharmacological techniques have been developed. The least invasive and most promising treatment modality is the pharmacological approach. A preferred pharmacological approach involves the site-specific delivery of cytostatic or cytotoxic drugs directly to the stent deployment area. Site-specific delivery is preferred over systemic delivery for several reasons. First, many cytostatic and cytotoxic drugs are highly toxic and cannot be administered systemically at concentrations needed to prevent restenosis. Moreover, the systemic administration of drugs can have unintended side effects at body locations remote from the treatment site. Additionally, many drugs are either not sufficiently soluble, or too quickly cleared from the blood stream to effectively prevent restenosis. Therefore, administration of anti-restenotic compounds directly to the treatment area is preferred.

Several techniques and corresponding devices have been developed to deploy anti-restenotic compounds including weeping balloon and injection catheters. Weeping balloon catheters are used to slowly apply an anti-restenotic composition under pressure through fine pores in an inflatable segment at or near the catheter's distal end. The inflatable segment can be the same used to deploy the stent or a separate segment. Injection catheters administer the anti-restenotic composition by either emitting a pressurized fluid jet, or by directly piercing the artery wall with one or more needle-like appendage. Recently, needle catheters have been developed to inject drugs into an artery's adventitia. However, administration of anti-restenotic compositions using weeping and injection catheters to prevent restenosis remains experimental and largely unsuccessful. Direct anti-restenotic composition administration has several disadvantages. When anti-restenotic compositions are administered directly to the arterial lumen using a weeping catheter, the blood flow quickly flushes the anti-restenotic composition down stream and away from the treatment site. Anti-restenotic compositions injected into the lumen wall or adventitia may rapidly diffuse into the surrounding tissue. Consequently, the anti-restenotic composition may not be present at the treatment site in sufficient concentrations to prevent restenosis. As a result of these and other disadvantages associated with catheter-based local drug delivery, investigators continue to seek improved methods for the localized delivery of anti-restenotic compositions. The most successful method for localized anti-restenotic composition delivery developed to date is the drug-eluting stent.

In one embodiment of the present invention, a implanted medical device is provided with a polymer coating containing an agonist of the angiotensin-(1-7) receptor. The present inventors have surprisingly shown that the local administration of the agonist Ang-(1-7) from the surface of an implanted medical device significantly improves impaired vascular endothelial cell function.

Amphiphilic polymers compatible for coating vascular stents according to the methods of the present invention include, but are not limited to, the copolymers described in co-pending U.S. patent application No. 10/970,171 filed Oct. 21, 2004, which is hereby incorporated by reference in its entirety. The amphiphilic copolymers of the Ser. No. 10/970,171 application are useful for coating medical devices with peptide drugs.

The amphiphilic copolymers have the general structure of Formula 1 wherein a, b and n are independently integers from 1–100 and n is the length of the PEG tail; $R_1$ is H or lower alkyl and $R_2$ is H, substituted or unsubstituted $C_1$–$C_{100}$ straight or branched chain alkyl, alkenyl, cycloalkyl, or cycloalkenyl groups, substituted or unsubstituted phenyl or benzyl group, heterocyclic groups, multi-cyclic alkyl or alkenyl groups, including, without limitation norbornyl and adamantyl groups. Substituent groups may include, but are not limited to halogens, hydroxyl groups, carboxyl groups, alkoxy groups, oxygen, nitrogen, sulfur, phosphorous, gallium, iron, boron and one or more radioisotope of same.

Formula 1

One of these amphiphilic copolymer, a copolymer of PEG-methacrylate and cyclohexyl methacrylate designated C45 was used to coat stents with Ang-(1-7).

The controlled release coatings of the present invention can be applied to medical device surfaces, either primed or bare, in any manner known to those skilled in the art. Application methods compatible with the present invention include, but are not limited to, spraying, dipping, brushing, vacuum-deposition, and others. Moreover, the controlled release coatings of the present invention may be used with a topcoat and/or a primer coat. A topcoat as used here refers to the outermost coating layer applied over another coating. A drug-releasing copolymer coating is applied over the primer coat. A polymer topcoat is applied over the drug-releasing copolymer coating. The topcoat may optionally serve as a diffusion barrier to further control the drug release, or provide a separate drug. The primer coat can be any biocompatible polymer such as parylene which is applied to the bare surface of the stent to protect the stent and have no effect on elution rates.

Figure 1:
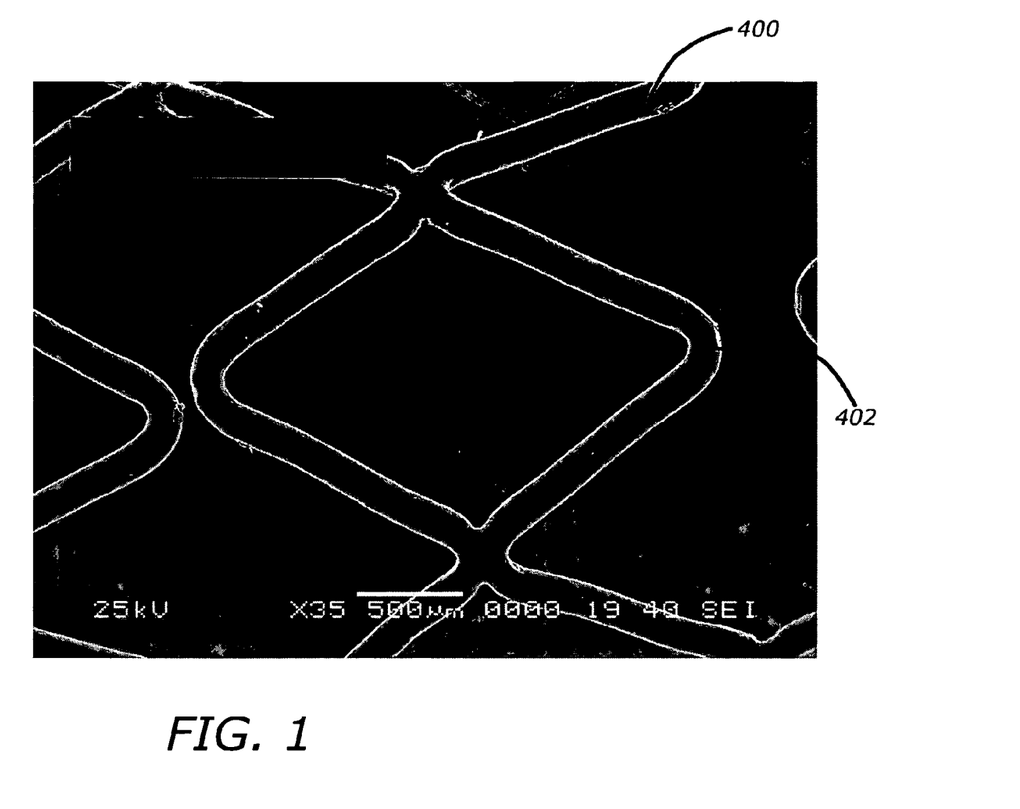
FIG. 1 depicts a vascular stent used to deliver the anti-restenotic compounds of the present invention.
Figure 2:
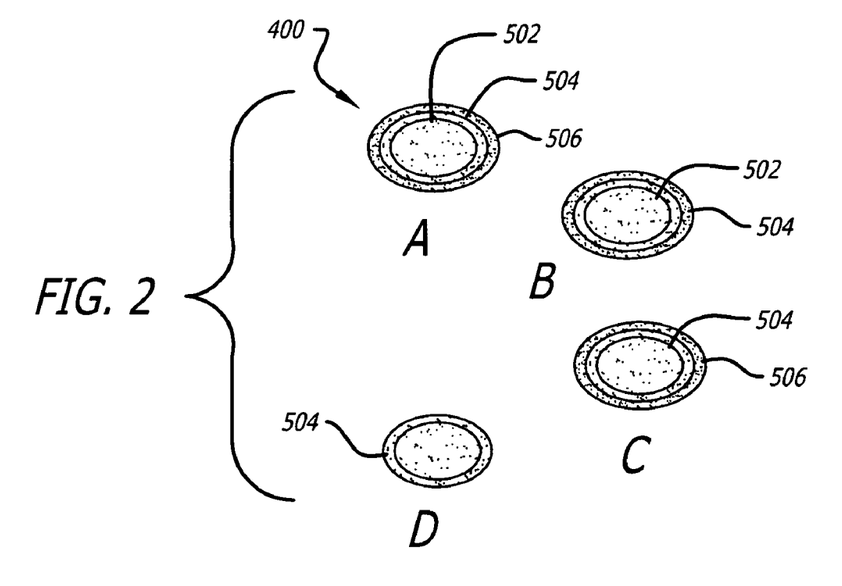
Figure 3:
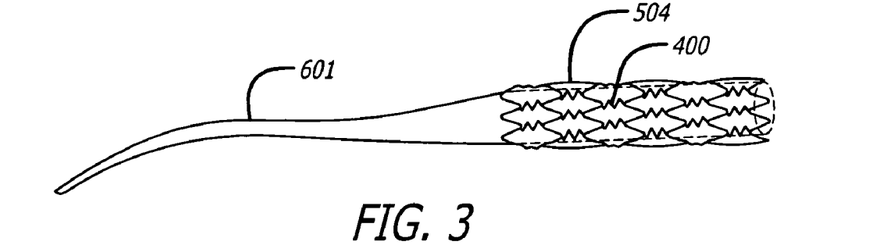
FIG. 3 depicts a balloon catheter in the retracted position (balloon deflated) according to the principles of the present invention where the shaft is mounted on an intravascular catheter.

One embodiment of the present invention is depicted in FIG. 1. In FIG. 1 a vascular stent 400 having the structure 402 is made from a material selected from the non-limiting group materials including stainless steel, nitinol, aluminum, chromium, titanium, ceramics, and a wide range of synthetic polymeric and natural materials including collagen, fibrin and plant fibers. The structure 402 is provided with a coating composition made in accordance with the teachings of the present invention. FIG. 2a–d are cross-sections of stent 400 showing various coating configurations. In FIG. 2a stent 400 has a first polymer coating 502 comprising an optional medical grade primer, such as but not limited to parylene; a second controlled release coating 504; and a third barrier, or topcoat 506. In FIG. 2b stent 400 has a first polymer coating 502 comprising an optional medical grade primer, such as but not limited to parylene and a second controlled release coating 504. In FIG. 2c stent 400 has a first controlled release coating 504 and a second barrier, topcoat 506. In FIG. 2d stent 400 has only a controlled release coating 504. FIG. 3 depicts a vascular stent 400 having a coating 504 made in accordance with the teachings of the present invention mounted on a balloon catheter 601.

The examples are meant to illustrate one or more embodiments of the invention and are not meant to limit the invention to that which is described below.

EXAMPLE 1

Angiotensin-(1-7) Pump Study in Rat Aorta Model

The effects of Ang-(1-7) on restenosis were studied in rats with uncoated stents implanted in the abdominal aorta with Ang-(1-7) infused by implantable micro pump. Twelve rats per group were implanted with stents and micropumps containing one of three infusion regimens for three weeks. Control rats received saline infusions and the Ang-(1-7) groups received infusion of Ang-(1-7) at 10 μg/kg/hr or 24 μg/kg/hr.

TABLE 1

Results of Rat Aorta Pump Study

| Group | Mean Injury Score | Media Area (mm$^2$) | Neointimal area (mm$^2$) | Percentage Stenosis (%) | Neointimal Thickness (mm) |
|---|---|---|---|---|---|
| Control | 0.93 ± 0.07 | 0.47 ± 0.04 | 0.70 ± 0.07 | 13.9 ± 1.3 | 141 ± 11 |
| Ang-(1–7) 24 μg/kg/hr | 1.11 ± 0.16 | 0.40 ± 0.05 | 0.51 ± 0.05* | 10.4 ± 1.0** | 111 ± 8 |

*p = 0.035;
**p = 0.016 vs. control

Figure 7:
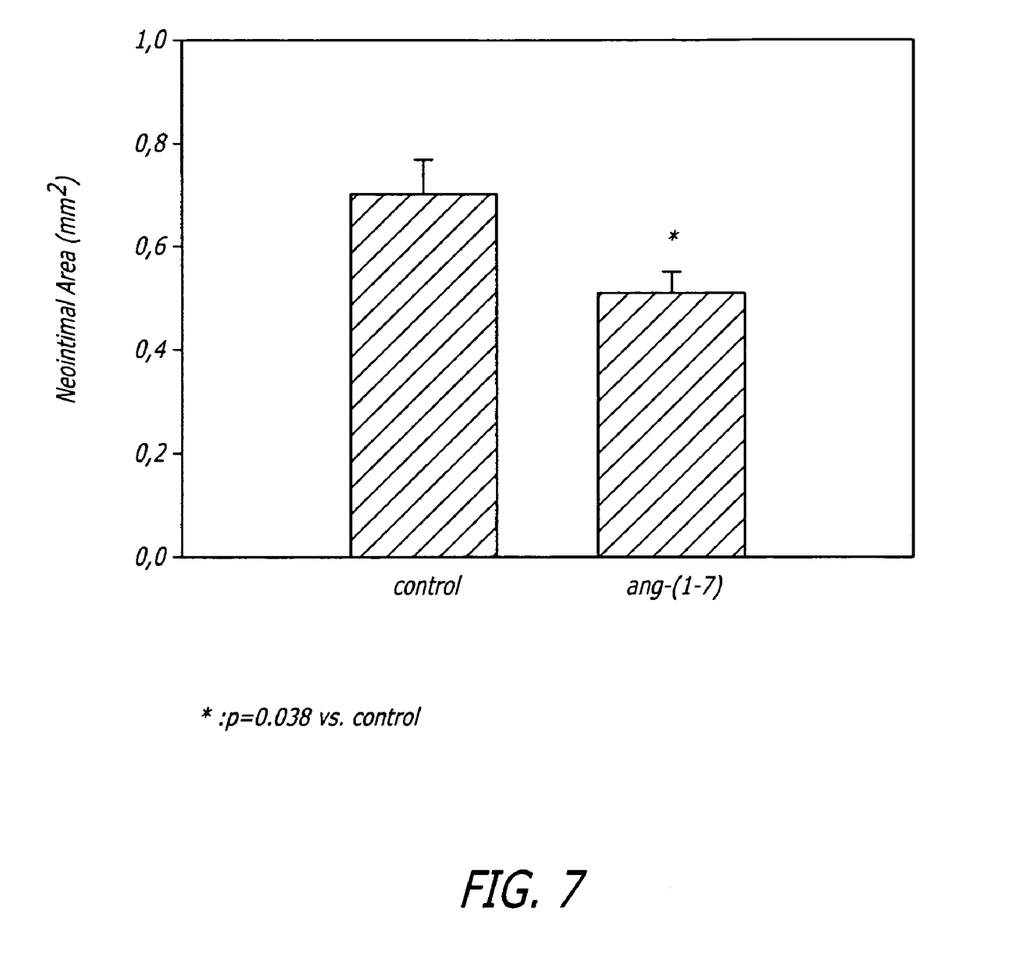
FIG. 7 depicts the effect of Ang-(1-7) infusion on neotintimal area after implantation of bare stents.

Rats that received a lower infusion level of Ang-(1-7), 10 μg/kg/hr, did not show any significant difference compared to the control group in any of the parameters measured. The rats receiving 24 μg/kg/hr, however, scored lower in neointimal level and percentage stenosis (Table 1 and FIG. 7). A 27% reduction in neointimal area was seen between the control rats and those receiving 24 μg/kg/hr Ang-(1-7). Ang-(1-7) has a clear beneficial effect on the restenosis rate. Additionally, results of this study indicated that Ang-(1-7) infusion improved endothelial function as measured in the thoracic aorta position, proximal from where the stent was placed.

EXAMPLE 2

Design of Angiotensin-(1-7) Eluting Stent

The design of an Ang-(1-7) eluting stent comprised a first layer of an amphiphilic copolymer containing 10–20% by weight of Ang-(1-7) and optionally a second coating (topcoat). The optional topcoat provides an additional barrier capable of providing sustained release of Ang-(1-7).

An amphiphilic PEG methacrylate-cyclohexyl methacrylate copolymer (designated C45, see co-pending U.S. patent application Ser. No. 10/970,171) was dissolved in methanol (MeOH) at room temperature overnight while shaking to a concentration of approximately 0.5% (wt/vol). Ang-(1-7) was added to the dissolved copolymer so that concentrations of 10% to 20% by weight of Ang(1-7) relative to C45 were achieved.

The C45/Ang-(1-7) solution was sprayed on 8 mm Medtronic Driver stents using standard spraying equipment in which the copolymer solution was vaporized ultrasonically. Coating weights were approximately 150 μg to 600 μg per stent. The optional topcoat contained no Ang-(1-7) and can be copolymers including, but not limited to, C45 or poly(butyl methacrylate) (PBMA). Coating weights were between 60 μg and 400 μg per stent.

EXAMPLE 3

Release of Angiotensin-(1-7) from C45 Coated 8 mm Stents in Vitro

For an in vivo study of Ang-(1-7) release from coated stents implanted in rat aortas, a series of 8 mm stents was prepared. For the release study, 8 mm stents were coated with C45 loaded with 20% by weight Ang-(1-7) applied as a 0.5% (wt./vol.) solution in MeOH with a coating weight of 150 μg. The topcoat was C45 (60 μg to 300 μg, applied from chloroform). The results of the in vitro release study are presented in FIG. 4. The release tests were performed in triplicate in phosphate-buffered saline (PBS) (pH 7.4) at 37° C. for periods up to 28 days. The stents were incubated in 750 μL of PBS containing sodium azide and at specific times the stents were removed from the PBS and the releasing media was analyzed for Ang-(1-7) using standard fluorescence techniques.

Figure 4:
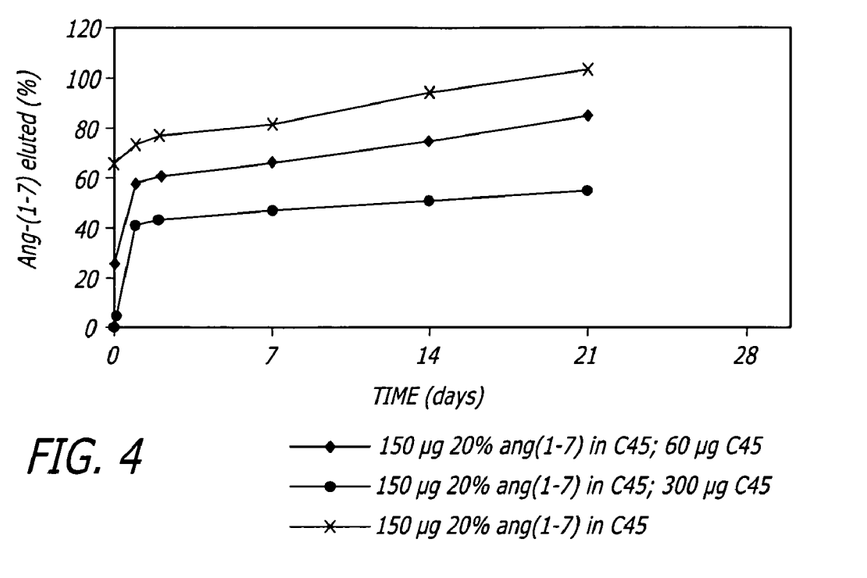
FIG. 4 graphically depicts in vitro release kinetics of 8 mm stents coated with C45-Ang-(1-7) and C45 cap coat according to the methods of the present invention.

The stents with no topcoat demonstrated a 70% burst and a sustained release for a few weeks. The release rate at day 21 was approximately 0.4 μg/day (FIG. 4). The effect of applying a C45 topcoat is also depicted in FIG. 4; the burst was suppressed and the release rate decreased from 0.4 μg/day to 0.1 μg/day at day 21. Additionally the coated stents performed well physico-mechanically; after crimping and expansion no cracks or loss of adhesion were observed.

Figure 5:
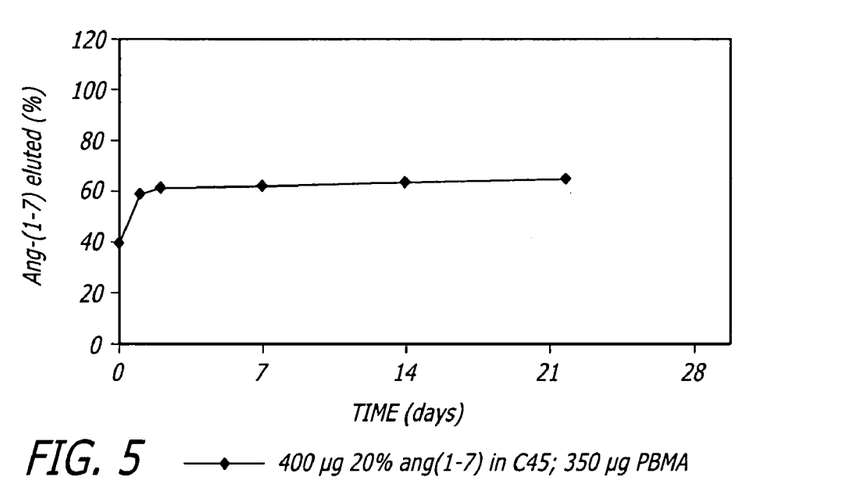
FIG. 5 graphically depicts in vitro release kinetics of Ang-(1-7)-coated stents implanted in rat aortas that were constructed according to the methods of the present invention.

For additional in vitro release studies, S8 Micro-Driver™ stents of 8 mm×2.5 mm were coated with 400 μg C45 containing 20% by weight Ang-(1-7) and a topcoat of 350 μg PBMA. The release profile of these stents is depicted in FIG. 5. These stents demonstrated a significant burst followed by controlled continuous release for 21 days at a rate of 0.2–0.3 µg/day from day 7 until day 21.

EXAMPLE 4

Release of Angiotensin-(1-7) from C45 Coated 15 mm Stents In Vitro

For an in vivo study of Ang-(1-7) release from coated stents implanted in pig aortas, a series of 15 mm stents was prepared. In vitro release studies for these stents were conducted essentially the same as for the 8 mm stents.

Figure 6A:
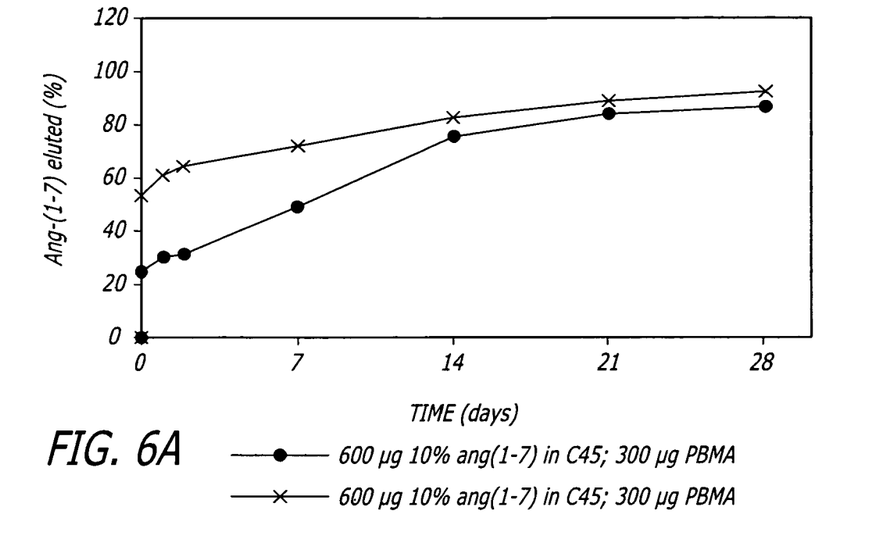
Figure 6B:
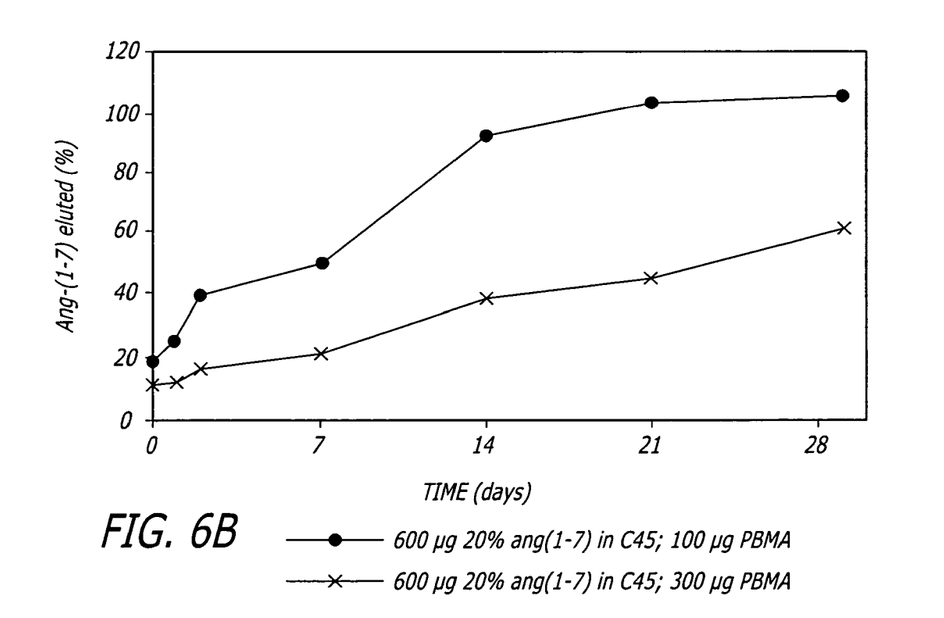

The stents were coated with 300 µg or 600 µg of C45 loaded with 10% or 20% by weight Ang-(1-7) and a topcoat of 100 µg to 400 µg PBMA. The in vitro release results (FIG. 6a) demonstrated a release rate of up to 2 µg/day of Ang-(1-7). Based on these results, two stents were selected for the pig study; a fast-releasing stent with 600 µg C45 with 10% by weight Ang-(1-7) and a 100 µg PBMA topcoat, and a slow-releasing stent with the same Ang-(1-7)-containing layer and a 300 µg PBMA topcoat. The in vitro release results for these two stents are depicted in FIG. 6b.

EXAMPLE 5

In Vivo Evaluation of Angiotensin-(1-7) Coated Stents in a Rat Aorta Model

The Ang-(1-7) coated 8 mm stents developed in Example 3 were implanted in the abdominal aorta of male Wistar rats (approximate weight 260 g). Each rat was anesthetized and the abdominal aorta prepared and the stent placed using a standard driver balloon catheter system. Three groups of rats are studied: bare stents, C45-only stents and C45-Ang-(1-7) coated stents.

Twenty-eight days post-implantation, animals underwent angiography as described above and were then sacrificed. Prior to sacrifice, BrdU injections were given to each animal at 24 hours prior to euthanasia. The stented segments of the aortas were located with the guidance of the coronary angiography, then the heart and/or arteries were dissected and fixed by perfusion with 10% formalin.

For processing, the stented vessel segments were dehydrated in a graded series of ethanol and embedded in methylmethacrylate plastic. After polymerization, five millimeter sections from the proximal, mid and distal portions of each stent were cut. To assess edge effect on the native vessel, a 3 mm section of the native vessel from the proximal and distal end the stents was taken. Sections were cut from the stents on a microtome at four to five microns, then mounted and stained with hematoxylin and eosin and Elastic Van Gieson stains. All sections were examined by light microscopy for the presence of inflammation, thrombus and neointimal formation and vessel wall injury. Myocardial sections were taken from the anterior, lateral, posterior and septal walls of the left ventricle distal to the stent and from the anterior, lateral and posterior apical region of the left ventricle. Sections were cut at 4–6 microns, mounted and stained with hematoxylin and eosin and examined for the presence of infarct, thrombus and inflammation. Each artery was evaluated for various parameters related to trauma, thrombus formation and restenosis.

Morphometric analysis was performed for the following parameters: artery area, lumen area, intimal area, arterial diameter, percent occlusion and lumen/artery ratio. Arteries were assigned an injury score, an inflammation score and a smooth muscle cellularity score. The vessel injury score was calculated according to the Schwartz method (Schwartz, RS et al. J Am Coll Cardiol 19:267–274, 1992). The cross-sectional areas (external elastic lamina (EEL), internal elastic lamina (IEL) and lumen) of each section were measured with digital morphometry. Neointimal thickness was measured as the distance from the inner surface of each stent strut to the luminal border. Percent area stenosis was calculated with the formula [(neointimal area/IEL area)×100].

Figure 8A:
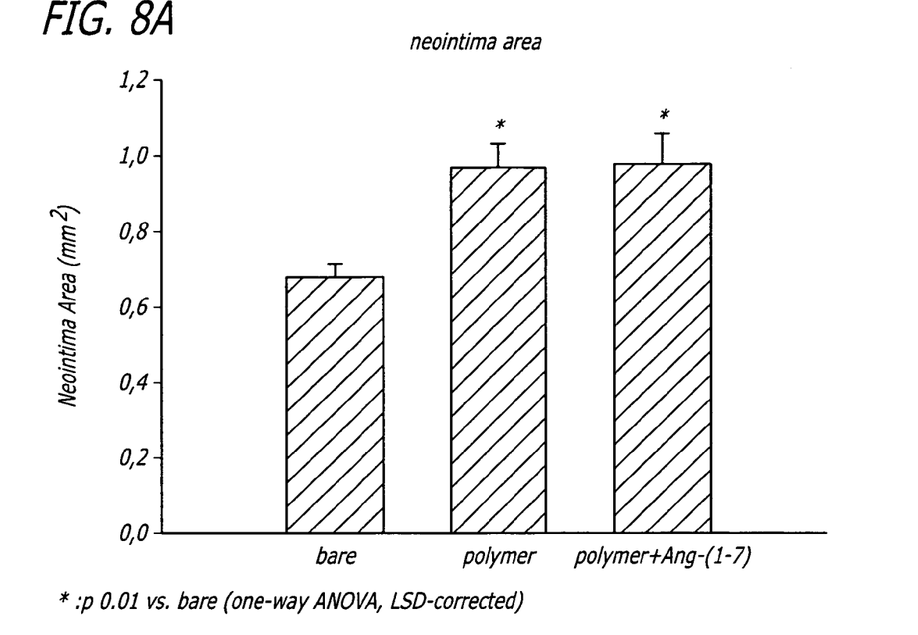
Figure 8B:
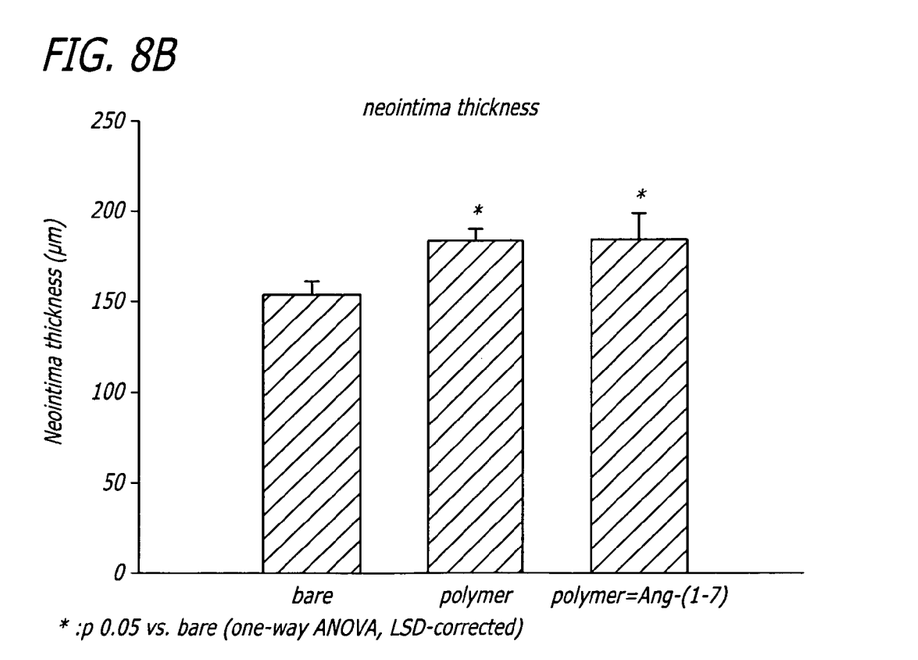
FIG. 8B, neointimal thickness) of stented areas of rat aortas after implantation of bare stents, C45-coated stents (polymer) and C45-Ang-(1-7) coated stents (polymer+Ang-(1-7)) according to the teachings of the present invention.

The effects of Ang-(1-7) coating of stents implanted on neotintima area and neointima thickness in rat aortas are depicted in FIGS. 8a and 8b.

Figure 9:
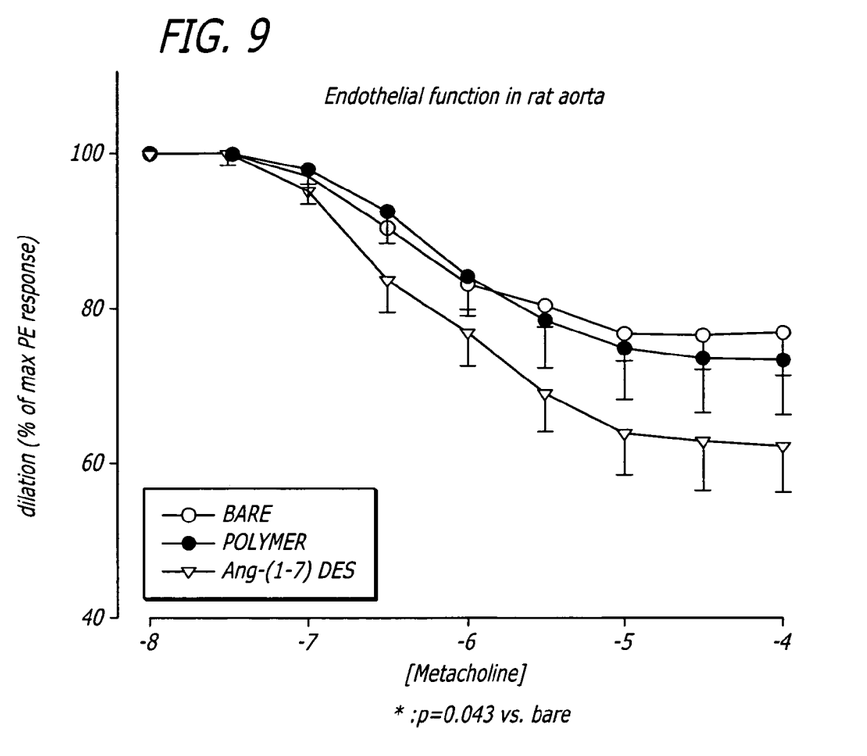
FIG. 9 depicts the endothelial function of rat aortas after implantation of bare stents, C45-coated stents (polymer) and C45-Ang-(1-7) coated stents (Ang-(1-7) DES) according to the teachings of the present invention.

To determine endothelial cell function, organ bath studies with isolated aortic rings were conducted. Peri-aortic tissue was removed from the aorta and rings of approximately 2 mm were cut. The rings were connected to an isotonic displacement transducer at a preload of 14 nM in an organ bath containing Krebs solution (pH 7.5) containing: 120.4 mM NaCl, 5.9 mM KCl, 2.5 mM $CaCl_2$, 1.2 mM $MgCl_2$, 1.2 mM $NaH_2PO_4$, 11.5 mM glucose, 25 mM $NaHCO_3$. The cultures were incubated at 37° C. and continuously gassed with 95% $O_2$ and 5% $CO_2$. After stabilization, during which regular washing was performed, the rings were checked for viability by stimulation with phenylephrine (PR, 1 mM). The rings were than washed and restabilized and sets of rings were precontracted with 1 mM phenylephrine. The endothelium-dependent vasodilation was assessed by a cumulative dose of metacholine (ME, 10 nM to 10 mM). Subsequently, the rings were dilated with the endothelium-independent vasodilator sodium nitrite (10 mM). The effects of stent implantation in the rat abdominal aorta on endothelial cell function were examined in the aortic rings taken proximally from the stent position (FIG. 9). Surprisingly, stenting with an Ang-(1-7) coated drug-eluting stent (Ang-(1-7) DES) resulted in significant improvement in vasodilatory response to ME as compared to the bare and polymer alone (polymer) coated stents. These results reveal a systemic improvement in endothelial function in the Ang-(1-7) DES group and indicate a supplementary therapeutic effect that can be achieved with Ang(1-7) DES above and beyond only an anti-restenosis effect.

EXAMPLE 6

In Vivo Evaluation of Angiotensin-(1-7) Coated Stents in a Pig Coronary Artery

The stents developed in Example 4 were then evaluated in vivo in a pig coronary artery system. Yorkshire pigs were implanted in the left anterior descending, left circumflex and right coronary arteries with different stents so that 8 stents from each group were evaluated. The experimental groups were: bare stent, C45-coated stent without drug, C45-Ang-(1-7) fast release stent and C45-Ang-(1-7) slow release stent.

Following overnight fasting, the pigs were sedated with a combination of ketamine (25 mg/kg), xylazine (2 mg/kg) and acepromazine (0.2 mg/kg) by intramuscular injection. Animals were intubated and ventilated with oxygen (2 L/min), and isoflurane 1–3% (1.5 L/min). Adequate anesthesia was confirmed by the absence of a limb withdrawal reflex. Limb-lead electrocardiography and blood pressure and heart rate were monitored throughout the procedure. All animals were pretreated with aspirin 325 mg/kg and Procardia XL® (75 mg) 24 hours prior to the procedure and Plavix® (75 mg) 3 days before the procedure. Aspirin (325 mg, once a day) and Plavix® (75 mg, once a day) were given orally throughout the study time.

The carotid area was shaved and scrubbed and carotid arteriotomy was performed. After placement of an introducer sheath in the carotid artery by surgical cutdown, each animal received a single dose of heparin IV (300 units/kg). Under fluoroscopic guidance, a guiding catheter was positioned in the left or right coronary ostium. Coronary angiography was performed and recorded on cinefilm (Philips Cardiodiagnost).

Stents were deployed in the left anterior descending, left circumflex and right coronary artery. The stent to artery ratio was kept between 1.1–1.2. The position of the stent was documented by cine video and by drawing and detailed description of the exact anatomic location of the stent.

Following stent implantation, the delivery catheter was removed, the carotid artery ligated and the cut down site closed with sutures. The animals were kept under observation until they have recovered from anesthesia. Nitroglycerin (30 mg), 600,000 unit of penicillin IM, 3000 units of heparin, Buprenex® IM (0.001–0.006 mg/kg) and fentanyl (25 µg) were administered before the animals were returned to routine care. After the procedure, the animals were maintained on aspirin 325 mg and Plavix 75® mg the entire time period until sacrifice.

Twenty-eight days post-implantation, animals underwent angiography as described above and were then sacrificed. Prior to sacrifice, BrdU injections were given to each animal at 24 hours prior to euthanasia. The stented segments of the coronary arteries were located with the guidance of the coronary angiography, then the heart and/or arteries dissected and fixed by perfusion with 10% formalin.

For processing, the stented vessel segments were dehydrated in a graded series of ethanol and embedded in methylmethacrylate plastic. After polymerization, five millimeter sections from the proximal, mid and distal portions of each stent were cut. To assess edge effects on the native vessel, a 3 mm section of the native vessel from the proximal and distal end the stents was taken. Sections were cut from the stents on a microtome at four to five microns thickness, then mounted and stained with hematoxylin and eosin and Elastic Van Gieson stains. All sections were examined by light microscopy for the presence of inflammation, thrombus and neointimal formation and vessel wall injury. Myocardial sections were taken from the anterior, lateral, posterior and septal walls of the left ventricle distal to the stent and from the anterior, lateral and posterior apical region of the left ventricle. Sections were cut at 4–6 microns thickness, mounted and stained with hematoxylin and eosin and examined for the presence of infarct, thrombus and inflammation. Each artery was evaluated for various parameters related to trauma, thrombus formation and restenosis.

Quantitative angiographic readings obtained from the single "worst view" projection were obtained at baseline, just after balloon injury or stent placement, and time of sacrifice. The analysis was done using the contrast filled guiding catheter as the reference standard, the reference diameter and minimal lumen diameter were obtained using a validated, computer-assisted automated edge-detection system (CMS, MEDIS). From these measurements, the mean minimal lumen diameters (MLD) at baseline and at follow up were calculated for the control and the treated coronary arteries.

Figure 10:
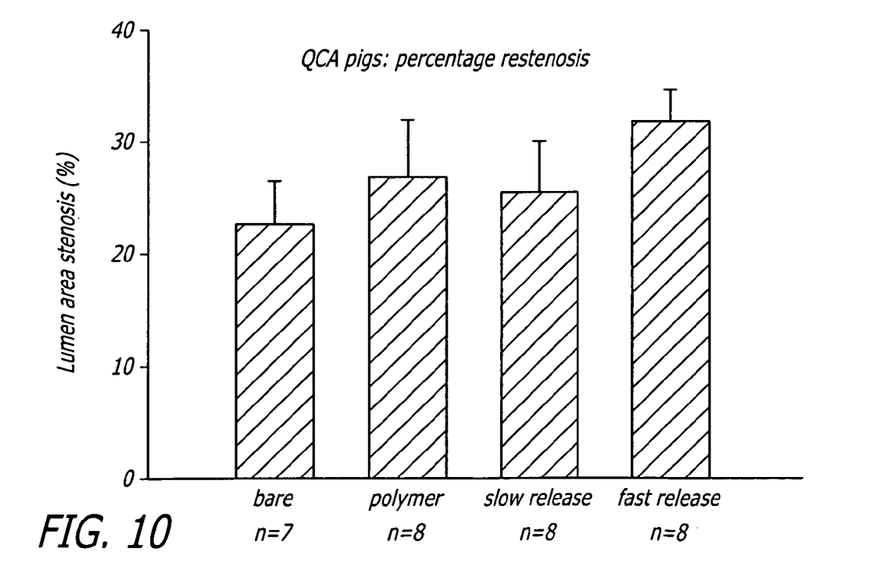
FIG. 10 depicts quantitative coronary angiography of pig coronary arteries after implantation of bare stents, C45-coated stents (polymer), slow-release C45-Ang-(1-7) coated stents (slow release) and fast-release C45-Ang-(1-7) coated stents (fast release) according to the teachings of the present invention.

The percent restenosis of the pig coronary arteries was determined by quantitative coronary angiography (QCA) and depicted in FIG. 10. Percent lumen area stenosis was calculated as [(reference vessel diameter—minimum lumen diameter)/reference vessel diameter]×100. Percent restenosis was improved in stents coated with the slow release formulation of C45-Ang-(1-7) over the stents coated with the fast release formulation of C45-Ang-(1-7).

Morphometric analysis was performed for the following parameters: artery area, lumen area, intimal area, arterial diameter, percent occlusion and lumen/artery ratio. Arteries were assigned an injury score, an inflammation score and a smooth muscle cellularity score. The vessel injury score was calculated according to the Schwartz method (Schwartz R. S. et al. J. Am. Coll. Cardiol. 19:267–274, 1992). The cross-sectional areas (external elastic lamina (EEL), internal elastic. lamina (IEL) and lumen) of each section were measured with digital morphometry. Neointimal thickness was measured as the distance from the inner surface of each stent strut to the luminal border. Percent area stenosis was calculated with the formula [(neointimal area/IEL area)× 100].

Figure 11A:
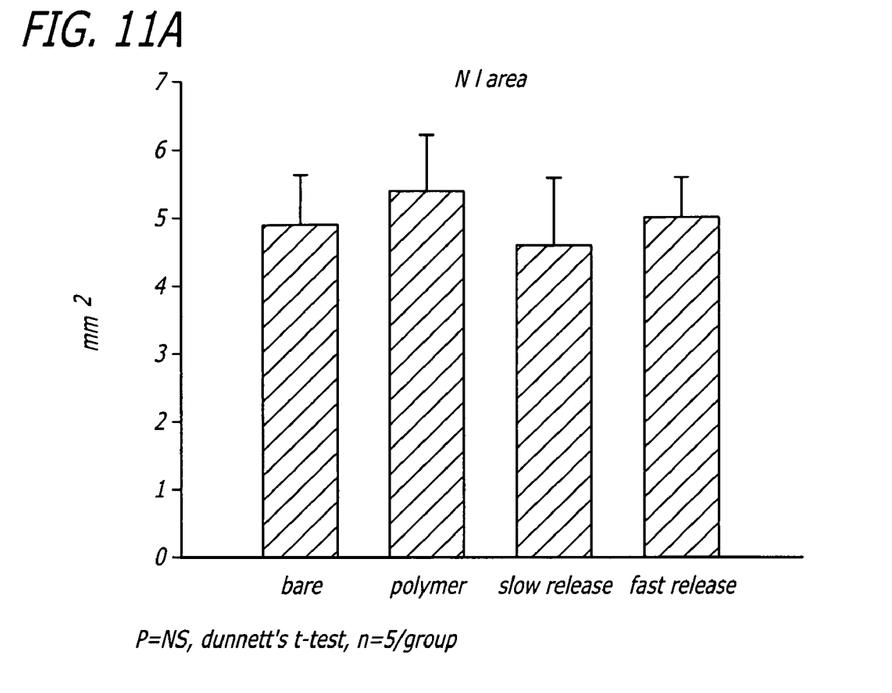
Figure 11B:
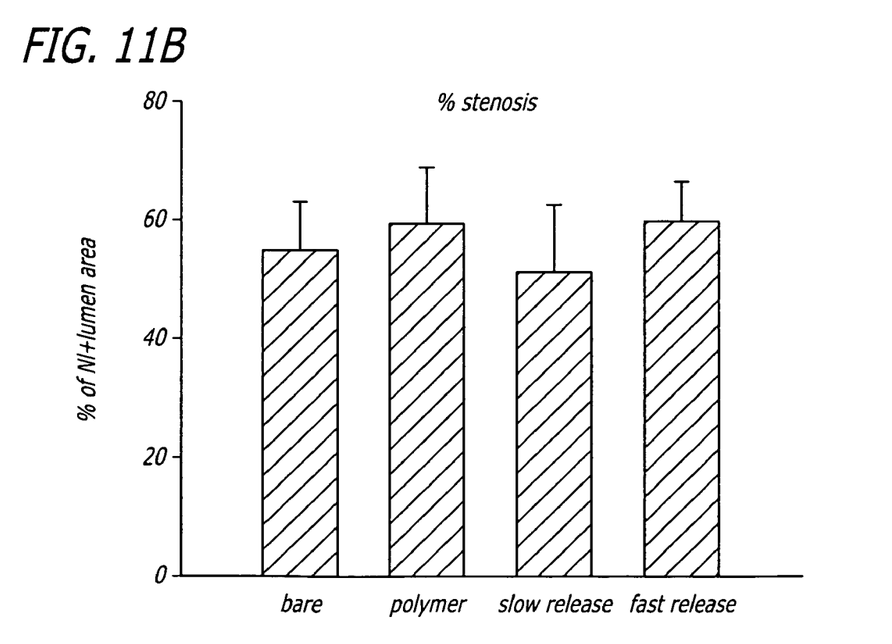

The morphometric analysis of the pig coronary arteries demonstrated similar results to that seen with the QCA results. FIG. 11 depicts neointimal area (FIG. 11a) and percent stenosis (FIG. 11b) of pig coronary arteries after implantation with the four stent types. Both neointimal area and percent stenosis were slightly improved in stents coated with the slow release formulation of C45-Ang-(1-7) over the stents coated with the fast release formulation of C45-Ang-(1–7).

Delivery of Ang-(1-7) from drug eluting stents may provide benefits both in prevention of in-stent restenosis and improvement of endothelial function.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A medical device comprising: a stent having a generally cylindrical shape comprising an outer surface, an inner surface, a first open end and a second open end; a controlled-release coating comprising an amphiphilic copolymer comprising a PEG methacrylate-cyclohexyl methacrylate copolymer and at least one angiotensin-(1-7) (Ang-(1-7)) receptor agonist; wherein at least one of said inner or outer surfaces deliver an effective amount of said at least one Ang-(1-7) receptor agonist to a tissue of a mammal.

2. The medical device of claim 1 wherein said at least one Ang-(1-7) receptor agonist is a peptide having the amino acid sequence of SEQ ID NO. 1.

3. The medical device of claim 1 wherein said stent is a vascular stent.

4. The medical device of claim 1 wherein said at least one Ang-(1-7) receptor agonist is present on both said inner surface and said outer surface of said vascular stent.

5. The medical device of claim 1 wherein said vascular stent further comprises a primer coat.

6. The medical device of claim 1 wherein said medical device further includes a polymer topcoat comprising a PEG methacrylate-cyclohexyl methacrylate copolymer or poly (butyl methacrylate).

7. The medical device of claim 1 wherein said vascular stent further comprises both a primer coat and a polymer topcoat.

8. The medical device of claim 2 wherein said peptide is in a concentration of between approximately 0.1% to 99% by weight of peptide-to-polymer.

9. A vascular stent for inhibiting restenosis in a mammal comprising: stent having a generally cylindrical shape comprising an outer surface, an inner surface, a first open end and a second open end; a controlled-release coating comprising a PEG methacrylate-cyclohexyl methacrylate copolymer and an anti-restenotic amount of an Ang-(1-7) receptor agonist peptide having the amino acid sequence of SEQ ID NO. 1; and a methacrylate copolymer topcoat; wherein said vascular stent delivers an effective amount of said Ang-(1-7) receptor agonist to a tissue of a mammal.

10. The vascular stent of claim 9 wherein said vascular stent further comprises a primer coat.

11. A method for inhibiting restenosis in a mammal comprising: a vascular stent having a controlled-release coating thereon wherein said coating comprises an amphiphilic copolymer comprising a PEG methacrylate-cyclohexyl methacrylate copolymer and an effective amount of at least one Ang-(1-7) receptor agonist at a treatment site; and inhibiting restenosis in said mammal.

12. The method according to claim 11 wherein said at least one Ang-(1-7) receptor agonist is a peptide having the amino acid sequence of SEQ ID NO. 1.

13. The method according to claim 12 wherein said peptide is in a concentration of between approximately 0.1% to 99% by weight of peptide-to-polymer.

14. The method according to claim 11 wherein said vascular stent has a generally cylindrical shape comprising an outer surface, an inner surface, a first open end and a second open end and wherein at least one of said inner or outer surfaces are coated with said controlled-release coating.

15. The method according to claim 11 wherein said vascular stent further comprises a primer coat.

16. The method according to claim 11 wherein said vascular stent further includes a polymer topcoat comprising a PEG methacrylate-cyclohexyl methacrylate copolymer or poly(butyl methacrylate).

17. The method according to claim 11 wherein said vascular stent further comprises both a primer coat and a polymer topcoat.

18. A method for improving endothelial cell function in a mammal comprising: implanting a vascular stent having a controlled-release coating thereon wherein said coating comprises an amphiphilic copolymer comprising a PEG methacrylate-cyclohexyl methacrylate copolymer and an effective amount of at least one Ang-(1-7) receptor agonist at a treatment site; and improving vascular endothelial cell function in said mammal.

19. The method according to claim 18 wherein said at least one Ang-(1-7) receptor agonist is a peptide having the amino acid sequence of SEQ ID NO.1.

20. The method according to claim 19 wherein said peptide is in a concentration of between approximately 0.1% to 99% by weight of peptide-to-polymer.

21. The method according to claim 18 wherein said vascular stent has a generally cylindrical shape comprising an outer surface, an inner surface, a first open end and a second open end and wherein at least one of said inner or outer surfaces are coated with said controlled-release coating.

22. The method according to claim 18 wherein said vascular stent further comprises a primer coat.

23. The method according to claim 18 wherein said vascular stent further includes a polymer topcoat comprising a PEG methacrylate-cyclohexyl methacrylate copolymer or poly(butyl methacrylate).

24. The method according to claim 18 wherein said vascular stent further comprises both a primer coat and a polymer topcoat.

25. A method for treating impaired vascular endothelial cell function in a mammal comprising: implanting a stent having a controlled release coating and an effective amount of Ang-(1-7) disposed on at lease one surface of said medical device at a treatment site in a vessel lumen, wherein said controlled release coating comprises a PEG methacrylate-cyclohexyl methacrylate copolymer; releasing said Ang-(1-7) from said surface of said stent such that vascular endothelial cell function is improved at said treatment site.

26. The medical device of claim 1 wherein said medical device improves vascular endothelial cell function and/or inhibits restenosis.

27. The vascular stent of claim 9 wherein said vascular stent improves vascular endothelial cell function and/or inhibits restenosis.

* * * * *

UNITED STATES PATENT AND TRADEMARK OFFICE
CERTIFICATE OF CORRECTION

| | |
|---|---|
| PATENT NO. | : 7,176,261 B2 |
| APPLICATION NO. | : 11/256582 |
| DATED | : February 13, 2007 |
| INVENTOR(S) | : Edze Jan Tijsma, Anita Driessen-Levels and Marc Hendriks |

Page 1 of 1

It is certified that error appears in the above-identified patent and that said Letters Patent is hereby corrected as shown below:

Col. 18, Line 38  "comprising: a vascular" should read --comprising: implanting a vascular--

Signed and Sealed this

Twenty-fifth Day of December, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 7
<212> TYPE: PRT
<213> ORGANISM: Homo sapiens

<400> SEQUENCE: 1

Asp Arg Val Tyr Ile His Pro
1               5